United States Patent [19]
Bridgman

[11] 3,939,835
[45] Feb. 24, 1976

[54] MEDICAL ASPIRATION SYSTEM VACUUM LEVEL INDICATOR

[76] Inventor: Henry Bridgman, P.O. Box 71, Convent Station, N.J. 07961

[22] Filed: July 3, 1974

[21] Appl. No.: 485,335

Related U.S. Application Data

[62] Division of Ser. No. 258,960, June 2, 1972, Pat. No. 3,833,000.

[52] U.S. Cl. ............................. 128/276; 116/114 C
[51] Int. Cl.² .................... A61M 1/00; G01L 21/00
[58] Field of Search ......... 116/114 C, 114 P, 114 S; 73/37, 388 R; 128/276

[56] References Cited
UNITED STATES PATENTS

| | | | |
|---|---|---|---|
| 2,040,798 | 5/1936 | Schoonmaker | 116/114 C |
| 2,295,528 | 9/1942 | Cutter et al. | 73/388 R |
| 3,143,111 | 8/1964 | Green | 73/37 X |
| 3,173,372 | 3/1965 | Baldwin | 73/37 X |

FOREIGN PATENTS OR APPLICATIONS

| | | | |
|---|---|---|---|
| 863,289 | 7/1949 | Germany | 116/114 C |
| 749,526 | 5/1943 | Germany | 116/114 P |

*Primary Examiner*—Richard C. Queisser
*Assistant Examiner*—Daniel M. Yasich
*Attorney, Agent, or Firm*—Roland Plottel

[57] ABSTRACT

A medical aspiration system vacuum level indicator. The system preferably to be used for vacuum abortions and diagnostics. It is designed for operation at high vacuum and includes an aspiration collection bottle. The vacuum level indicator comprises an expandable non-porous membrane charged with a predetermined quantity of gas. The membrane is positioned inside the collection bottle, and provides a visual indication of the vacuum level in the bottle.

2 Claims, 2 Drawing Figures

MEDICAL ASPIRATION SYSTEM VACUUM LEVEL INDICATOR

This is a division of Application Ser. No. 258,960 filed June 2, 1972 now U.S. Pat. No. 3,833,000.

The invention relates generally to medical aspiration equipment. The invention will find particular application in uterine aspiration such as vacuum abortions or sampling of tissue for endometrial cancer detection.

Within the past years a technique called uterine aspiration or vacuum curettage has been developed for performing abortions during the early months of pregnancy. The earliest reference to this technique appeared in an article by Y. T. Wu and H. C. Wu, entitled "Suction in Artificial Abortion-300 Cases" in the Chinese Journal of Obstetrics and Gynecology, Vol. 6, 1958, beginning at page 447. A recent survey of the subject appeared in an article by Kerslake and Casey, entitled, "Abortion Induced by Means of Uterine Aspirator" in Obstetrics and Gynecology, Vol. 30, July, 1967, pages 35–45. Very briefly, the technique described in the Kerslake and Casey article is to aspirate and conceptus from the uterus using a tube which has a flexible connection to a source of suction. A typical apparatus as described in the article includes a suction curette having an oval mouth at its end, or on one side, and an air hole at the other end to control the suction. A rubber suction tubing connects the curette to a glass container which in turn is connected to a source of suction. Aspiration of the uterine contents usually takes less than two minutes and the fetal material can readily be seen as it appears in the glass container. The method employed may be very briefly reviewed. The perineum, vagina, and cervix are disinfected. The cervix is then drawn forward with a tenaculum. The direction of the cervical canal and the depths of the uterine cavity are determined with a uterine sound. It is a common practice to dilate the cervix to allow easy insertion of the suction curette. When dilation is required, preferably a local anesthesia is administered. General anesthesia is rarely used. The suction curette of appropriate diameter and design is inserted carefully through the cervix into the uterus. The suction is then started. In a few seconds the suction reaches a working level which, according to the Kerslake and Casey article, is at a mean level of 18 inches of mercury (relative). The suction curette is moved gently up and down over all aspects of the uterine cavity. The products of conception pass visibly into the glass container either whole or piecemeal. The degree of suction can be controlled with some aspirators by putting a thumb over an airhole at the base of the curette as well as by using a pressure control device on the pump. During the aspiration process, the uterus reacts by contracting and decreasing in volume. Aspiration usually takes less than a minute or two. It is thought to be complete when the uterine wall feels smooth and no further remnants emerge. A typical prior art apparatus used for uterine aspiration consists of a curette connected by a hose to a collection bottle which in turn is connected by a second hose to a vacuum source.

In the prior art system described by Kerslake and Casey the source of the vacuum or suction, the collection bottle, and the curette or cannula, are connected by hoses or pressure tubing. The working level of vacuum or suction typically is 15 to 18 inches of mercury (relative) and is gradually raised to this level after the curette is inserted into the uterus.

Uterine aspiration, is not limited to abortions, but is a general technique with a further application in diagnostics. For example, in a recent article by B. A. Bjerre, et al, entitled "Aspiration Curettage — a New Diagnostic Method" in the Journal of Reproductive Medicine, Vol. 7, No. 5, November, 1971, the technique of aspiration curettage was recommended for routine use in collecting tissue for endometrial diagnosis and other diagnostic purposes. Here the curette is of a small outside diameter, typically 3mm, welded to a plastic cap of a tubular chamber which in turn is connected to a suction pump. The plastic chamber contains a perforated plastic cylinder that serves as a filter and arrests mucosal fragments which are to be laboratory tested for either polyps, endometrial "atypia", or an adenocarcinoma. The technique employed in the diagnostic aspiration curettage is similar to that employed for the abortions by vacuum curettage. Here the vagina and portico are cleaned, typically with soap. The portico is gripped with a tenacucoum forceps; a uterine sound is passed in the cervix and without further dilation the curette is advanced into the fundus. Suction is introduced and the curette is passed over the entire uterine wall; tissue and some blood is scraped from the uterine wall and aspirated by suction. The tissue is trapped in the tubular chamber and a histopathological examination is subsequently done on the aspirated and trapped tissue.

In one embodiment a high vacuum is used, e.g. 28 to 30 inches of mercury, which is applied with full strength at the very beginning of the procedure. By using this high vacuum, it is possible to construct an aspiration system in which the collection bottle, source of vacuum, and handle for the curette are all one. This does away with a separate source of suction, whether that be an electric pump (which is commonly used in the United States), or a vacuum jar (as used in China). It might be noted that electric pumps are subject to failure — due to electrical interuptions, or to accidental carry-over of fluids from the collection bottle — with the very serious consequence that the procedure is interupted and has to be completed by sharp D & C or in extreme cases by a hysterectomy. The system of the invention, moreover, does away with the prior art hoses which connect the curette to the collection bottle and the collection bottle to the suction source. These hoses encumber the physician. Furthermore, if the curette is not provided with a handle and swivel, which are heavy, it is difficult to rotate the curette in the uterus. This feature is considered very desirable by many surgeons. In the present invention there are no encumbering hoses, and the surgeon may rotate the curette easily without heavy swivels or other attachments.

In one embodiment of the invention, a high vacuum is induced in a transparent bottle typically less than one-half liter in volume. A cap with a valve is mounted on this bottle and a cannula or curette rigidly fits into a seat on the valve. In a typical procedure, the cannula is introduced into the uterus, the valve is then opened and the full vacuum rapidly sucks the products of conception from the interior of the uterus. The surgeon may grasp the bottle in one or both of his hands and move the cannula tip over the wall of the uterus. The valve is then closed, and the apparatus is withdrawn.

It will be noted that the apparatus is relatively small. The volume of a typical bottle is 0.35 liters, small enough to be conveniently held in a surgeon's hand. This size is possible because of (1) the initial high vacuum and (2) the absence of hoses, which dilute residual vacuum by reason of expansion, and (3) the discovery that the material extracted from the uterus is a fluid with virtually no gas content. The latter point might be examined a little more fully. The products of conception extracted from the uterus is a fluid with entrained semi-solids. This apparently was not previously appreciated, nor was it applied to the practical design of uterine aspiration apparatus. Experimentation has confirmed that the collection bottle may be filled approximately 70% full with aspirated material before the pre-induced vacuum level falls more than 12%. (In one measurement, a 475 milliliter container starting with an initial vacuum of 28.64 inches of mercury was filled to 400 milliliters and had a remaining vacuum of 26.85 inches of mercury. When subsequently filled to 450 milliliters, it still had 23.34 inches of mercury vacuum). The important point is that it is not until the aspirated volume reaches about 70% of collection bottle volume that the initial induced vacuum begins to deteriorate appreciatly. This fact apparently had not been appreciated nor was it applied heretofore to uterine aspiration systems.

A further advantage of this system is that the aspirated products may be easily observed by the physician because the collection bottle is attached directly to the cannula and is in his hand during the procedure. In prior art abortion systems the collection bottle is remotely positioned. When connected by a hose, the collection bottle — in order to avoid being accidentally toppled over when the hose was pulled on — is securely mounted onto a stable platform which is usually some distance away and the physician has to look up and away from the patient and the point of operation to see the aspirated material. With the apparatus of the present invention, the doctor applies his sense of touch to the collection bottle, and also concentrates visually on the collection bottle to observe the products of conception being removed.

A further advantage, is lack of dependence on the electric vacuum pump. In addition to mechanical failure, possible contamination, and electric power failure, the pump has the further drawback in that its noise is psychologically upsetting and stress-producing on the patient. It has been observed that when the pump is turned on and running, the patient reacts with an undesirable tension, complicating the emotional, as well as the physical completion of the operation. The system of the present invention it will be noted is completely silent.

It may be noted that this embodiment has the further advantages of being compact in that it occupies but a small volume, and it is simple to assemble, disassemble and clean as well as to operate.

The initial vacuum in the bottle of this system may be induced by an electric pump, or by any other means.

Other objects and features of the invention disclosed will become apparent to those skilled in the art upon reference to the following specifications and accompanying drawings wherein several embodiments are disclosed by way of illustration.

IN THE DRAWINGS

Figure 1:
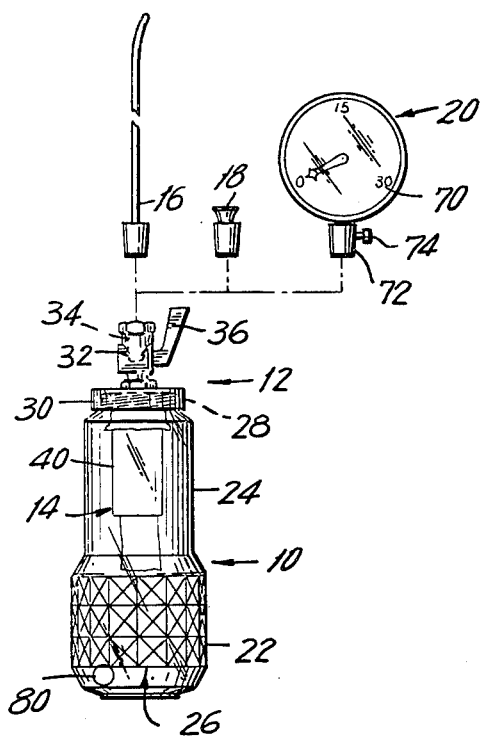
FIG. 1 is a plane view of a preferred embodiment of the invention, and auxiliary apparatus that may be used therewith.

Referring now to the drawing of FIG. 1, there is shown a preferred embodiment of a collection apparatus of the invention, which will find typical application in terminating early pregnancies. The apparatus consists basically of three parts: a collection vacuum bottle, 10, a cap valve socket assembly, 12, and a mesh filter or trap, 14. A cannula, 16, fits directly into a socket connection of the cap valve socket assembly, 12. Two accessories are also shown in FIG. 1. The first is a floating relief and check valve, 18, which may be used when the vacuum in the collection bottle is to be produced thermodynamically, as described more fully below. The second, is a test gauge, 20, to measure the vacuum in the collection bottle, and which is more fully described below.

The collection bottle itself, 10, is preferably made of a clear (i.e. transparent) heat resistent material (e.g. Pyrex). The dimensions of the collection bottle are such that it may be conveniently hand-held. A preferred bottle has a lower portion, 22, which is larger than its upper portion, 24. A checkered or textured surface, 26, may be provided on the lower portion, 22, of the bottle, to facilitate gripping. A typical bottle is 6½ inches long, with the upper portion 2¼ inches in diameter and the lower portion 2½ to 3 inches in diameter. During a procedure the bottle is held in one hand and manipulated. Alternatively, the surgeon may loosely hold the upper portion in one hand, and graps the lower portion with his other hand, swivelling the apparatus so as to move the cannula tip over the wall of the uterus. It should be noted that the assembled apparatus includes the cannula rigidly connected to the collection bottle so that the bottle in addition to being the collection chamber, and the resevoir of the vacuum, is also the handle for the cannula. It should be further noted that the collection bottle during the procedure is in the hands of the surgeon and the extracted products of conception can be readily viewed through its transparent walls by the doctor as he performs the operation.

The upper end of the bottle terminates in a screw fitting, 28, which mechanically mates with a corresponding fitting on the cap valve socket assembly, 12. It should be understood, however, that any convenient or convenitonal fitting may be used so long as the connection is vacuum tight, and for certain embodiments, are also heat resistent.

The cap valve socket assembly, 12, includes a cap portion, 30, which connects to the screw thread, 28, on the upper portion of the bottle. A plug valve, 32, is mounted on the cap, 30, and terminates in a suction curette socket connection, 34. The cannula or curette, 16, fits directly into the socket connection, 34, and is secured tightly therein by either a friction fit, as is common with many curettes commercially available, or by any other convenient or conventional securing means. The plug valve, 34, includes a handle, 36, which is movable between first and second positions to permit, or to block, a freeflow having at least ⅜ inches diameter passage from the socket connection at 34, to the interior of the bottle at the inside of the cap, 30.

The mesh filter or trap, 14, may be a rigid plastic or metal mesh strainer which fits inside the collection bottle, and may be attached either to the inner face of the cap, or along the interspace between the cap and the top lip of the bottle. In practice, the traps collect the fetal parts and other solid material which are subsequently examined by the surgeon or pathologist. In the case of endometrial tissue collection, it is this tissue material which is sought for the subsequent diagnostic testing. In the case of abortion the semi-solid material is examined to make sure all of the products of conception have been removed.

In a typical procedure, the trap, 14, is connected and the cap assembly, 12, is attached to the bottle, 10 (with the handle, 36, in the open position). Vacuum is induced inside the bottle, 10, the handle, 36, is closed A sterile cannula, 16, is fitted into the socket, 34; and the apparatus is ready for the procedure. After the patient has been prepared, the cannula is introduced into the uterus, and the surgeon opens the valve, 34, at the handle, 36; and then, by manipulating the bottle, 10, with one or both hands, moves the opened end of the cannula over the surface of the uterus wall, extracting the conceptus. When all the material is believed to be removed, the handle, 36, is closed, and the apparatus is removed. In the case of endometrial tissue extraction, a similar routine is followed.

The vacuum inside the bottle, 10, may be produced immediately before the operation, by an electrical or mechanical pump. Alternatively the apparatus may be vacuum pre-packaged with the vacuum induced several weeks or months before the procedure and the apparatus rests on the shelf until ready.

It has been discovered that the aspirated products have very little, if any, gaseous content, and the high vacuum pre-induced inside the collection bottle remains relatively stable until approximately 70% has been filled with liquid and semi-solid material! For example, with an initial vacuum of 28.43 inches of mercury a collection bottle was filled 73% full and the remaining vacuum was still 25 inches of mercury.

The relationship can be generalized and expressed mathematically as follows:

$$Pr = \frac{PaVf + Ps(V-Va)}{Vf + (V-Va)}$$

Where

Pr = Pressure (vacuum remaining in collection bottle for any amount of fluid volume aspirated).
Ps = Initial pressure in collection bottle (pre-induced vacuum).
Pa = Atmospheric pressure.
V = Volume of collection bottle.
Vf = Free volume between suction tip opening and valve.
Va = Fluid volume aspirated.
All Expressed in Absolute Units.

Figure 2:
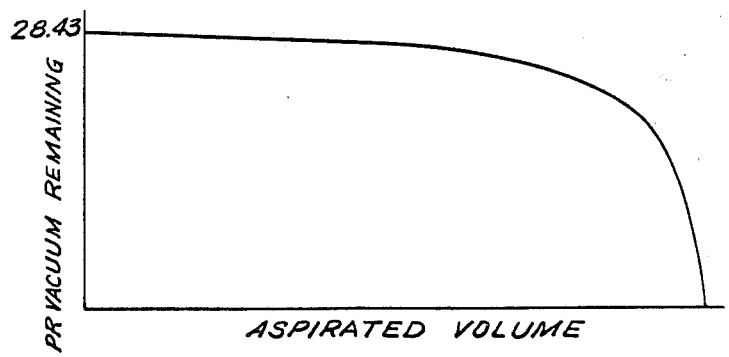
FIG. 2 is a graph illustrating the relation between pressure (vacuum) remaining in the bottle in terms of fluid volume aspirated.

In the apparatus of the present invention the quantity Vf (the free volume between the suction tip opening on the cannula and the valve) is held to a minimum because there are neither hoses nor intermediate connections between the cannula and the valve to deplete the available vacuum. When Pr, (the vacuum remaining in the collection bottle) is expressed in terms of Va (the fluid volume aspirated) for any set of given conditions, it is found that Pr does not change appreciably until the fluid volume aspirated reaches about 70% of the collection bottle volume. Thus, relatively large volumes of fluid may be aspirated at nearly constant pre-induced vacuum levels. This relationship is shown graphically in FIG. 2.

A further accessory for use with the apparatus is shown in FIG. 1. It is the vacuum test gauge, 20, which has a conventional vacuum gauge, 70, connected to a lower mating plug, 72, which fits into the socket, 34. The available vacuum can be measured without the loss of any pressure, (other than the vacuum associated with the gauge, 20, which is negligable) by placing the plug, 72, in the socket, 34, and opening the handle, 36. The gauge, 20, is also provided with a bleeder control knob, 74, which permits the controlled introduction of ambient air into the collection bottle. With this arrangement the vacuum inside the bottle may be adjusted to a lower level, if desired, while monitoring the remaining pressure on the gauge, 70.

An alternative gauge, 80, is shown in FIG. 1. It will find particular application with pre-packaged vacuums that may remain on the shelf for several weeks or months. Gauge 80, is a non-porous elastic membrane, filled with a given quantity of gas. It is positioned inside the bottle, 10. When there is vacuum in the bottle, the membrane is completely inflated through the expansion of entrapped air sealed in at atmospheric pressure. As the vacuum decreases, the membrane correspondingly collapses. Thus, the size of the membrane, 80, provides a rough indication of the amount of vacuum remaining in the bottle. During a procedure, as the vacuum bottle fills, the gauge, 80, provides a continuous measure of remaining vacuum. This is possible because it is light and floats on top of any collected liquids, and is always readily visible.

Although the invention has been described with examples applicable to abortions, it is not so limited, and may find application elsewhere. For example, where the apparatus is to be used for endometrial cancer detection, or for removal of cysts and drain other body cavities, different sized cannula, and different sized collection bottles may be used. For example for endometrial testing the cannula typically has an outside diameter of 3 mm (this may be contrasted with the cannula used in the early weeks of pregnancy of approximately 6 to 8 mm) and the collection bottle is small in size, typically having a volume of about 100 ml.

Thus there has been shown and described a uterine aspiration system which is self-contained, easy to use and frees the doctor from the encumbrances of connecting hoses, swivels, etc. Furthermore, the collection bottle forms the "handle" of the curette and thus not only provides a good support, but also permits inspection of the extracted products during the procedure. The apparatus of the invention moreover, does not depend upon an electric pump as its source of vacuum during the operation, and thus is free from the noise, and the resulting psychological stress associated therewith and possibility of power failure. There has also been explained that it is possible to perform the vacuum curettage with a relatively small volume high vacuum collection bottle There has also been described various gauges, and accessory valves, for use with the apparatus of the present invention.

What is claimed is:

1. A vacuum level indicator for use in an evacuated empty medical uterine aspiration collection bottle comprising an expandable non-porous elastic membrane positioned inside said collection bottle and adapted to be used with means for regulating the introduction of material from the uterus into said evacuated bottle, said bottle being transparent to permit viewing of said indicator, said membrane defining an enclosed volume inside said evacuated bottle, a predetermined quantity of gas within said enclosed volume sufficient to provide a first visually observable expansion of said elastic membrane when said bottle is empty and evacuated, and a different expansion when said bottle is either substantially filled with aspirated material or when said bottle is no longer evacuated.

2. A medical uterine aspiration system indicator comprising a transparent collection bottle having a volume in the range of 50 to 500 milliliters; a cap for said bottle; an operator operative valve mounted in said cap and adapted to be connected to a cannula, said valve providing on/off or flow through passage from said portion connectable to said cannula and to the interior of said bottle; said bottle, cap, and valve when closed being hermetically tight and capable of withstanding when evacuated a high vacuum within said bottle; an expandable non-porous membrane extending inside said bottle, sealing off a portion of the space inside said bottle, said sealed-off portion being charged with a predetermined quantity of gas; said membrane expanding due to the presence of said gas when said bottle is evacuated, and contracting to a readily observable different indication when said bottle is filled to more than seventy percent of its capacity by aspirated uterine liquids and semi-solids.

* * * * *